United States Patent
Kristensen

(10) Patent No.: US 6,890,331 B2
(45) Date of Patent: May 10, 2005

(54) ELECTROSURGICAL APPARATUS

(75) Inventor: Tom Kristensen, Hellerup (DK)

(73) Assignee: XO Care A/S, Hørsholm (DK)

(*) Notice: Subject to any disclaimer, the term of this patent is extended or adjusted under 35 U.S.C. 154(b) by 90 days.

(21) Appl. No.: 10/148,127

(22) PCT Filed: Sep. 28, 2001

(86) PCT No.: PCT/DK01/00621
§ 371 (c)(1),
(2), (4) Date: May 28, 2002

(87) PCT Pub. No.: WO02/26146
PCT Pub. Date: Apr. 4, 2002

(65) Prior Publication Data
US 2002/0183737 A1 Dec. 5, 2002

(51) Int. Cl.$^7$ ............................................. A61B 18/04
(52) U.S. Cl. ........................... 606/32; 606/34; 606/37; 606/38; 606/41; 606/42
(58) Field of Search ........................ 606/32–34, 37–42

(56) References Cited

U.S. PATENT DOCUMENTS

| 4,580,562 A | 4/1986 | Goof et al. |
| 5,188,122 A | 2/1993 | Phipps et al. |
| 5,720,744 A | 2/1998 | Eggleston et al. |
| 5,749,869 A | 5/1998 | Lindenmeier et al. |
| 5,957,969 A | 9/1999 | Warner et al. |
| 5,976,128 A | 11/1999 | Schilling et al. |
| 6,010,499 A | 1/2000 | Cobb |

FOREIGN PATENT DOCUMENTS

WO    WO 95 09577    4/1995

Primary Examiner—Rosiland Rollins
(74) Attorney, Agent, or Firm—Browdy and Neimark, P.L.L.C.

(57) ABSTRACT

An electrosurgical apparatus comprises a high frequency generator (1) with an associated power control system, a handpiece (2) with means for removably mounting an electrode (5) therein, and a connection cable (3) between an output (4) of the generator and the handpiece. The transfer characteristic of the system provides a substantially true ohmic transfer of loads on the electrode side of the connection cable (3) to the generator side thereof at or around a predetermined load on the electrode.

In order to achieve a fully automatic and optimalized control af power supplied from a cutting electrode, whereby the control is instantly responding, to changes in the electrode load, the electrosurgical apparatus is characterized in that the power control system comprises a driver stage (7) followed by a reflectormeter (9) adapted and arranged to sense the generator output (4). A detector (10) supplies a detector signal which represents the reflected signal on the output (4), and the detector signal is communicated to the driver stage (7) for controlling the gain thereof.

2 Claims, 1 Drawing Sheet

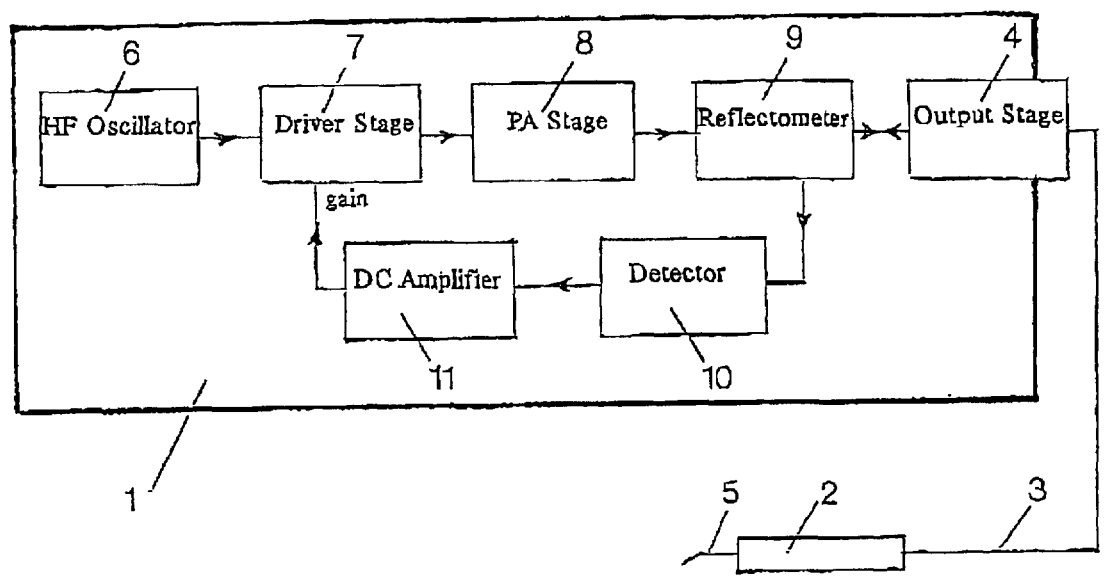

ELECTROSURGICAL APPARATUS

BACKGROUND OF THE INVENTION

1. Technical Field of the Invention

The present invention relates to an electrosurgical apparatus of the type which is used, in particular by surgeons and dentists, to perform incisions and also to stop bleeding.

2. Prior Art

Electrosurgical equipment of the type in question is based on a power generator which supplies a high frequency alternating current. Via a connection cable this current is conducted to an electrode—the so-called active electrode—which is replacably mounted in a handpiece. For dissections the active electrode is usually made of thin metal wire which remains cold because of good conductivity, but when the electrode is advanced through tissue, a local heating is generated in the tissue a. o. because of the electrical resistance of the tissue.

This heating causes a molecular dissolution of the tissue cells since the generated heat causes both intra- and extra-cellular generation of steam which bursts the tissue cells, and the result is a well-defined incision in the tissue. How deep this dissolution takes place in the tissue is depending a. o. on the current intensity and on the speed at which the electrode is advanced through the tissue. Normally the faces of incision are substantially free of bleeding, and the damages to adjacent tissues are at a minimum.

Because of the restraining effects to bleeding, the equipment can also be used specifically to stop bleeding. For that purpose the generator is usually switched to provide a modulated current waveform, and the result is a deeper coagulation necrosis relative to the electrode which usually is ball-shaped for that purpose. The result is an efficient hemostasis in connection with concentrated as well as more diffuse bleeding.

An important benefit of using electrosurgery instead of a scalpel is a substantially more precise incision and, moreover, the operating field remains clean, dry and without bleeding. This is an essential advantage e.g. in connection with the taking of impressions for tooth crowns and bridges, because an impression can be taken immediately after after that the necessary incisions have been made, Electrosurgery is also well-suited for pre-prosthetic surgery and for para-dontal surgery as well.

In electrosurgery one of the principal goals is to make clean cuts with a minimum of tissue destruction. This requires that the output power from a cutting electrode continously is precisely adapted to the type of tissue and to the amount of issue (the depth of cut) with which the electrode is in contact. At the same time the output power may at no instant be larger than necessary, because too large power delivery will result a.o. in unclean cuts and possibly also in sparkling between electrode and tissue which causes tissue necrosis and thereby complicates and prolonges the healing proces.

In particular the output power must be effectively and rapidly reduced as soon as a cutting electrode approaches the periosteum or bone tissue. Otherwise, the result would be very painful damages such as periostitis, bone necrosis and sequestration of bone tissue.

In other words, electrosugical equipment of the type under consideration for making incisions in living tissues must include very efficient means for continuous control or dosage of the power supplied by a cutting electrode, Moreover, such power control means must respond rapidly—virtually instantly—to changes in the electrical load of the electrode i.e. the conductivity or susceptance.

The electrical load is to an essential extent determined by two factors, namely the material resistance i.e. the inherent resistance of the tissue, and the conducting area i.e. the area of contact between electrode and tissue (the depth of cut).

Both factors may vary during a cutting operation. If for instance an electrode which is advanced at constant depth through soft tissue, approaches bone tissue, then there will be a sudden decrease in the load or susceptance experienced by the electrode, because bone tissue has a substantially higher electrical resistance than soft tissue due to the substantially lower contents of liquid in bone tissue. As already mentioned a very rapid reduction of the power supplied by the electrode must take place in such instances, because, otherwise, the result could be very painful damages to bone tissue or tooth substances.

If on the other hand the cutting depth of the electrode is suddenly decreased, then there will also be a sudden decrease in the load or susceptance due to the decreasing area of contact between tissue and electrode. The minimum load or susceptance which is zero, at least in principles, will occur when the electrode gets free the tissue—and thus is in the air. Again it is very important that the power from the electrode is decreased very rapidly, because otherwise the result could be sparkling and serious burning and destruction of tissue.

In conclusion, it is important that the power supplied by a cutting electrode is efficiently and rapidly decreased as soon as the load or susceptance experienced by the electrode is decreased for one reason or another.

DK patent No. 149 762 discloses an electrosurgical apparatus of the type under consideration and which provides an extremely rapidly and precisely responding control of the power output from the electrode as a function of the instant load on the electrode. This control has been achieved by using impedance matching techniques, and the system is matched or in tune at one quite specific load impedance which occurs when an electrode is cutting at maximum depth in soft tissue.

In or immediately around this particular matched condition, the output power from the electrode will accordingly be at its maximum, whereas the output power will be efficiently and rapidly decreased because of mismatching in all other conditions i.e. with decreasing depth of cut and/or with increasing electrical tissue resistance.

Thus, impedance matching technique has been utilized to deliberately mis-match the output stage in such a manner that the oscillation ability, and thereby the power output, is reduced as soon as the electrode load moves away from the particular condition with impedance matching. The result is an automatic and direct regulation in true time of the power output as a function of the instantaneous load and in such a manner that the power delivered to the tissue by a cutting electrode, continuously is adapted to the type of tissue and/or to the depth of cut.

However, in the electosurgical apparatus just described it has been seen that the regulation range for output power is not sufficiently broad to range—without further measures—all the way from cutting in the tissue surface without sparkling (minimum load) and up to cutting in full depth with maximum power (maximum load). It has therefor often been necessary to compromise either by renouncing on a part of the available maximum power in return of a completely sparkless operation, or by accepting some degree of sparkling in return of availability of the full maximum power.

OBJECT AND SUMMARY OF THE INVENTION

It is the object of this invention to remedy this drawback of the prior art apparatus by providing an electrosurgical apparatus of the same type with instantly responding power control based on impedance matching technique, but in which the complete range of regulation is constantly available.

The primary or continuous control of the output power during dissections takes place by means of the system known per se and which is based on impedance matching technique. This control takes place instantly and in dependence of the instantaneous electrical load on the electrode.

Concurrently herewith the apparatus of the invention is performing a continuous and automatic adjustment of the output power level, in as much as the gain of the driver stage automatically can be controlled to decrease, when the reflectometer is sensing that a major part of the output signal is being reflected—that is to say during incisions with small depths (low load). Hereby the sparkling can be controlled and efficiently prevented.

Correspondingly, the gain of the driver stage can be controlled to automatically increase when the reflectometer is sensing that only a minor part of the output signal is being reflected—that is to say during deep incisions (high load). Hereby the maximum power can be made fully available when making deeper incisions.

In other words the invention provides an optimized power characteristic, and the power control takes place in a fully automatic manner completely without the need of manual adjustments.

The invention will now be described in further details and with reference to the drawing which is a block diagram of an electrosurgical apparatus according to the invention.

BRIEF DESCRIPTION OF THE DRAWING

As shown schematically in the drawing the apparatus of the invention includes a generator part 1, a handpiece 2, and a connection cable 3 between the handpiece and an output 4 of the generator part.

DETAILED DESCRIPTION OF THE PREFERRED EMBODIMENTS OF INVENTION

The generator part 1 is based on a BP-oscillator 6 which preferably is a crystal controlled, 50 watt generator with an output frequency of 27.125 Mhz which is within a free transmission frequency range.

The oscillator 6 supplies a driver stage 7 which preferably is a 5 watt amplifier stage, and in the embodiment shown the driver signal is conducted to a PA-stage 8. In a preferred embodiment the PA-stage 8 includes a transformer which is phase splitting the driver sign by 180 degrees, and the resulting signal drives a following PA-stage, whereafter the power is combined in a following transformer.

The PA-stage 8 is followed by a directional coupler or a reflectometer 9 which is in communication with the output stage 4 which preferably includes a low-pass filter for reduction of the radiation of harmonics before the output signal is conducted to an output terminal.

The handpiece 2 includes means for replacably coupling of an electrode 5 which usually is a thin wire electrode which can be shaped in various ways in view of the contemplated use. Other more special electrodes may also be used e.g. for stopping bleeding.

By use of impedance matching techniques the system is tuned in such a manner that one quite specific electrical load on the electrode 5 will be transferred to the generator end of the cable 3 by a true ohmic transfer. Accordingly, the system is in tune or matched at that particular electrode load, and the power supplied by the electrode is consequently at its maximum, because the reflected part of the generator output signal is at a minimum.

At every other electrode load the power supplied by the electrode will be reduced because a bigger part of the generator output signal is being reflected due to mismatching.

The result is a continuous, automatic, and instantly responding control of the power supplied by a cutting electrode in dependence of the instantaneous electrical load encountered by the electrode.

The reflectometer 9 in the generator part 1 of the apparatus of the invention is currently sensing the instantaneously reflected part of the output signal, and a detector circuit 10 provides a detector signal which corresponds to the reflected signal part on the generator output 4. The detector signal wil accordingly vary with and represent the instantaneous load of a cutting electrode.

The detector signal from circuit 10 is utilized to control the gain in the driver stage 7, and preferably this takes place via a DC amplifier 11 designed to adjust or adapt DC level and gain.

Hereby a positive feed back has been provided by means of which the gain of the driver stage 7 is being regulated in dependence of the size of the reflected signal on the output which means in dependence of the instantaneous electrode load.

Accordingly and concurrently with the instantly responding power control based on impedance matching technique, there will be an automatic adjustment or setting of the level of the output power, in as much as the gain in driver stage 7 can be reduced to a desired extent at high values of the reflected signal (low electrode loads), whereby the signal level on the output will be correspondingly lower. The instantly responding power control is still going on to a fall extent, but consequently now at or around the lower or reduced power level.

Correspondingly the gain in driver stage 7 can be appropriately increased at low reflected signal values (high electrode loads), whereby the signal level on the output will be correspondingly higher. Again the instantly responding power control continues to a full extent at or around the higher or increased power level.

The result is an improved and optimized power control characteristic spanning over au expanded power range which extends all the way from quite law output powers and up to the maximum power which the generator is able to supply. Throughout the expanded range the power control is going on in a fully automatic manner and with extreme rapidness.

Consequently and without further measures the electrosurgical apparatus of the invention is able to operate without sparkling at quite low electrode loads (small depths of cut), and at the same time the maximum power is available to a full extent for making deep incisions.

What is claimed is:

1. An electrosurgical apparatus comprising
a high frequency generator (1) with an associated power control system; a handpiece (2) with means for removably mounting an electrode (5) therein; and a connection cable (3) between all output (4) of the generator and the handpiece (2);

wherein the transfer characteristic of the system provides a substantially true ohmic transfer of loads on the electrode side of the connecting cable to the generator side thereof at or about a predetermined load impedance on the electrode (5), characterized in that said power control system comprises a driver stage (7) followed by a reflectometer (9) adapted and arranged to sense the generator output (4); and in that a detector (10) is adapted and arranged to supply a detector signal representing the reflected signal on the generator output (4), whereby said detector signal is communicated to said driver stage (7) for controlling the gain thereof.

2. An apparatus as defined in claim 1, characterized in that said detector signal is communicated to said driver stage (7) trough a DC amplifier (11) arranged to adjust DC level and gain.

* * * * *

UNITED STATES PATENT AND TRADEMARK OFFICE
CERTIFICATE OF CORRECTION

PATENT NO. : 6,890,331 B2
APPLICATION NO. : 10/148127
DATED : May 10, 2005
INVENTOR(S) : Kristensen It is certified that error appears in the above-identified patent and that said Letters Patent is hereby corrected as shown below:

1) Column 3, line 44, "BP-oscillator" should read --HF-oscillator-- .

2) Column 4, line 39, "fall" should read --full-- .

3) Column 4, line 49, "au" should read --an-- .

4) Column 4, line 66, "all" should read --an-- .

Signed and Sealed this

Second Day of January, 2007

JON W. DUDAS
*Director of the United States Patent and Trademark Office*